(12) United States Patent
Szurmann et al.

(10) Patent No.: US 10,682,216 B2
(45) Date of Patent: Jun. 16, 2020

(54) DEVICE FOR SUPPORTING AND TRANSPORTING A GRAFT OR IMPLANT

(71) Applicant: Geuder AG, Heidelberg (DE)

(72) Inventors: Peter Szurmann, Saarbrücken (DE); Hartmut Fath, Wiesloch (DE)

(73) Assignee: Geuder AG, Heidelberg (DE)

( * ) Notice: Subject to any disclaimer, the term of this patent is extended or adjusted under 35 U.S.C. 154(b) by 0 days.

(21) Appl. No.: 15/536,337

(22) PCT Filed: Dec. 15, 2014

(86) PCT No.: PCT/DE2014/200717
§ 371 (c)(1),
(2) Date: Jun. 15, 2017

(87) PCT Pub. No.: WO2016/095884
PCT Pub. Date: Jun. 23, 2016

(65) Prior Publication Data
US 2017/0340428 A1 Nov. 30, 2017

(51) Int. Cl.
*A61F 2/14* (2006.01)
*A61F 2/00* (2006.01)
*A61F 9/00* (2006.01)

(52) U.S. Cl.
CPC ............ *A61F 2/0095* (2013.01); *A61F 2/142* (2013.01); *A61F 2/148* (2013.01); *A61F 9/0017* (2013.01); *A61F 2250/0091* (2013.01)

(58) Field of Classification Search
CPC ...... A61F 2/0095; A61F 2/149; A61F 9/0017; A61F 2250/0091; A61F 9/0026;
(Continued)

(56) References Cited

U.S. PATENT DOCUMENTS

| 6,605,093 | B1 * | 8/2003 | Blake | A61F 2/1664 |
| | | | | 606/107 |
| 8,162,953 | B2 * | 4/2012 | Dishler | A61F 2/148 |
| | | | | 606/107 |

(Continued)

FOREIGN PATENT DOCUMENTS

| DE | 2009050511 A1 | 4/2009 |
| DE | 202011106789 U1 | 11/2011 |

(Continued)

OTHER PUBLICATIONS

International Search Report for PCT/DE2014/200717 dated May 8, 2015.

(Continued)

*Primary Examiner* — Paul B Prebilic
(74) *Attorney, Agent, or Firm* — McDonnell Boehnen Hulbert & Berghoff LLP

(57) ABSTRACT

The aim of the invention is to ensure a secure support and/or a secure transport of a graft (4) or an implant. This is achieved by a device for supporting and transporting a graft (4) or implant, comprising a container (2) which can be filled with a medium (1), preferably a nutrient medium, and a receiving device (3) which can be arranged in the container (2) for the graft (4) or implant. The receiving device (3) has a receiving chamber (5) for the graft (4) or implant and two passages (6, 7) which lead to the receiving chamber (5), at least one of said passages (6, 7) being dimensioned for introducing and/or removing the graft (4) or implant into or out of the receiving chamber (5). The device also comprises a respective closure device (8, 9) for each of the two passages (6, 7), at least one of the closure devices (8, 9) being permeable for the medium (1). The invention further relates to a corresponding receiving device (3) and to a set comprising a corresponding device.

13 Claims, 5 Drawing Sheets

Figure 1:
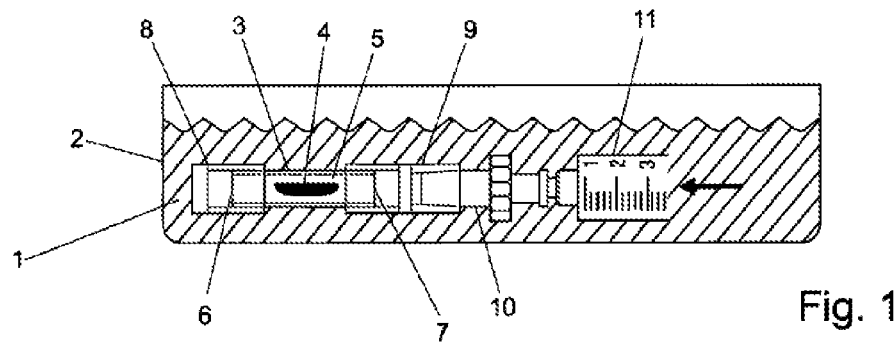

(58) Field of Classification Search
CPC ...... A61F 9/0061; A61F 9/007; A61F 9/0008; A61F 2220/0025; A61F 2230/0069; A61F 2250/0065; A61F 2/14
See application file for complete search history.

(56) References Cited

U.S. PATENT DOCUMENTS

| | | |
|---|---|---|
| 2003/0214139 A1 | 11/2003 | Nigam |
| 2006/0235430 A1 | 10/2006 | Le et al. |
| 2007/0208422 A1 | 9/2007 | Walter et al. |
| 2009/0270982 A1 | 10/2009 | Torres et al. |
| 2010/0211051 A1 | 8/2010 | Weston et al. |
| 2013/0023892 A1* | 1/2013 | Schneider ............... A61F 2/142 606/107 |
| 2013/0253527 A1* | 9/2013 | Schneider ............... A61F 9/007 606/107 |
| 2013/0253529 A1* | 9/2013 | Walter .................... A61F 2/142 606/107 |
| 2013/0261217 A1* | 10/2013 | Beyar ............... B01F 15/00876 523/116 |
| 2014/0288643 A1* | 9/2014 | Torres ..................... A61F 2/148 623/5.11 |

FOREIGN PATENT DOCUMENTS

| | | |
|---|---|---|
| DE | 10 2010 051458 A1 | 5/2012 |
| DE | 102010051458 A1 | 5/2012 |
| WO | 2005037136 A2 | 4/2005 |
| WO | 2009050511 A1 | 4/2009 |
| WO | WO 2012065602 A3 * | 5/2012 ............. A61F 2/167 |

OTHER PUBLICATIONS

Palioura, S. and Colby, K.: Outcomes of Descemet Stripping Endothelial Keratoplasty Using Eye Bank-Prepared Preloaded Grafts. Cornea Journal, vol. 36, No. 1, Jan. 2017.

* cited by examiner

DEVICE FOR SUPPORTING AND TRANSPORTING A GRAFT OR IMPLANT

This application is a U.S. National Phase Application pursuant to 35 U.S.C. § 371 of International Application No. PCT/DE2014/200717 filed Dec. 15, 2014. The entire disclosure contents of this application are herewith incorporated by reference into the present application.

The present invention relates to a device for supporting and transporting a graft or implant, comprising a container, which can be filled with a medium, preferably a nutrient medium, and a receiving device, which can be arranged in the container, for the graft or implant. The receiving device has a receiving chamber for the graft or implant and two passages, which lead to the receiving chamber, at least one of said passages being dimensioned for introducing and/or removing the graft or implant into or out of the receiving chamber. The device also comprises a respective closure device for each of the two passages, at least one of the closure devices being permeable for the medium. Preferably, for transporting both closure devices are impermeable for the graft or implant.

The invention further relates to a corresponding receiving device and a set comprising the above-mentioned device in sterilized condition or in a package suitable for sterilizing.

The transplantation of the human cornea is one of the most frequently and successfully performed transplantation-related surgical procedures. The transplantation of the cornea using all layers (epithelium, Bowman's membrane, stroma, Descemet's membrane and endothelial cell layer) in the context of perforating keratoplasty has been known for more than 100 years. Usually, this surgical method produces good results. However, convalescence is extremely slow and visual recovery can be ultimately achieved only after the second suture has been removed. This can involve a time period of up to 18 months after the surgical procedure.

More than half of all corneal transplants result from corneal endothelial diseases. For these diseases, a layer-specific replacement of the cornea would basically be suitable. Appropriate techniques for such replacements are currently available. Compared to perforating keratoplasty, it is possible since several years to achieve a faster visual recovery and, consequently, better patient satisfaction by transplanting the Descemet's membrane with an attached stroma lamellae (DSAEK).

An innovative, special form of corneal transplant has also been described for treating diseases of the cornea affecting the corneal endothelium. This involves Descemet's membrane endothelial keratoplasty (DMEK). In the course of such a surgical procedure, the diseased endothelial cells, including the underlying Descemet membrane, can be removed and replaced by a Descemet membrane with a healthy corneal endothelium of a donor. Perforating keratoplasty is not required. Instead, the graft can be transferred into the anterior eye chamber by means of a comparatively small incision and spread through very careful manipulation. The membrane preparation is then fixed by supplying air to the posterior stroma.

A successful DMEK surgery allows the patient to have a very fast visual rehabilitation. It can be assumed that the patient reaches full visual acuity approximately two months after the surgical procedure.

In general, quite a number of surgical and particularly ophthalmological procedures are known or conceivable in which a graft or implant is provided and inserted into the living body. In terms of a rapid convalescence of the patient, as described above in an exemplary manner by means of DMEK surgery, it is advantageous to introduce a graft or implant into the living body through an incision of limited size which is, in particular, as small as possible.

For example, DE 10 2010 051 458 A1 discloses a device for providing and introducing a graft or implant into the living body, particularly for ophthalmological procedures. The device described comprises a cartridge or sleeve with openings on its two opposite ends. Said cartridge or sleeve is especially suitable for introducing a graft or implant into the body of a patient through a very small incision, such as is required for the ophthalmological procedure described above.

For a successful medical application, it is also extremely important to provide a secure support and secure transport of the graft or implant. However, it is not only important to provide a secure support and secure transport of the graft or implant. It is also important to ensure that the graft or implant is transferred in a simple and secure manner from the support and/or transport situation to the location of surgical procedure. At the same time, damages and/or contaminations of the graft or implant have to be eliminated.

Therefore, the present invention is based on the objective of providing a device, a receiving device and a set comprising such a device, which allow for a secure support and/or secure transport, as well as a secure and simple provision of the graft or implant when it is to be introduced into the human or an animal body.

In an inventive manner, it has been recognized that an appropriately designed device can be suitable in an outstanding manner for supporting and transporting a graft or implant. For this purpose, the device comprises a container, which can be filled with a medium, preferably a nutrient medium, and a receiving device, which can be arranged in the container for the graft or implant. Consequently, the graft or implant is arranged in a separate receiving device in the container, and the receiving device comprises a receiving chamber for the graft or implant and two passages leading to the receiving chamber. At least one of said passages is dimensioned for introducing and/or removing the graft or implant into or out of the receiving chamber. The process of introducing and/or removing the graft or implant into or out of the receiving chamber takes place via the same passage. To be able to securely position the graft or implant in the receiving chamber, the device also comprises a respective closure device for each of the two passages. This ensures that the graft or implant does not pass over from the receiving chamber to the container, i.e., to the medium usually arranged in the container during a process of support and transport. As a result, the graft or implant is securely handled by means of the receiving device and, at the same time, the graft or implant secured in the receiving device is protected in the container. In an inventive manner, at least one of the two closure devices for the medium—not for the graft or implant—is also permeable. This allows for a safe contact between the graft or implant and the medium during the support and/or transport, because an adequate amount of medium can always pass through the permeable closure device into the receiving chamber and thus to the graft or implant. Within the framework of a special embodiment, one of the two closure devices can be formed through a constriction of the receiving device or a passage. In this respect, one of the two closure devices can be implemented as an integral component of the receiving device.

Because of the fact that the receiving device and the graft or implant arranged in the receiving device can be managed separately, the inventive device is perfectly suited to provide the graft or implant after a support and/or transport for a surgical application and thus for an introduction into a human or animal body.

As a result, the inventive device provides a device, which allows for a secure support and/or secure transport, as well as a secure and simple provision of the graft or implant to be introduced into the human or animal body.

In view of a particularly secure and simple provision of the graft or implant and in view of a particularly simple structural design of the receiving device, the receiving device can be designed in the form of a sleeve or cylinder. At the same time, the receiving chamber for the graft or implant is formed by the interior space of the sleeve or cylinder, and the two passages are formed by the opening at the ends of the sleeve or cylinder. Usually, these passages have the same dimensions, which means that the graft or implant can be introduced and/or removed into or out of the receiving chamber through both passages. In this respect, it is not necessary to pay attention to appropriately adjusting the receiving device for introducing and/or removing the graft or implant.

In a particularly simple and flexible manner, the closure devices can be mounted on the receiving device. This ensures a particularly simple manner of handling the device. Usually, the closure devices are mounted manually or with simple tools. Advantageously, the closure devices can be designed in the form of collars, which can be at least partially mounted or attached to the receiving device.

To position the closure devices on the receiving device in a simple manner, the closure devices can be configured from a slightly elastic material, preferably plastic material. Because of the elasticity of the material, the closure devices can be placed under pre-tension on the receiving device when it is dimensioned appropriately. It is possible to use the closure devices multiple times.

Basically, the closure devices can be designed in different ways. Besides closing the respective passage, the closure devices can have additional functions that can be implemented with the respective closure device. In an especially advantageous manner, at least one of the two closure devices, preferably both closure devices, can have a grid to provide the permeability for the medium. On the one hand, such a closure device provides a secure protection for the graft or implant positioned in the receiving chamber, preventing the graft or implant from accidentally escaping the receiving chamber. On the other hand, the closure device provides the required permeability for the medium, allowing the graft or implant to be adequately moistened or flushed by the medium. Both closure devices comprise such a grid so that the medium is introduced in a particularly safe manner into the receiving chamber and flushed through the receiving chamber. Advantageously, the grid can be an integral component of the respective closure device.

To be able to implement further functions, the receiving device or at least one of the two closure devices can be designed with a provision for connecting a collar or an adapter, or an integrated adapter or adapter area in such a way that it is possible to connect a tube, syringe, preferably a disposable syringe, or a device to supply and/or discharge the medium and/or a further fluid medium, preferably a staining solution. On the one hand, the receiving device can be designed with a provision for connecting a collar or an adapter, or an integrated adapter or adapter area. On the other hand, this adaption option can be provided by means of a closure device that is already connected with the receiving device. For example, the connection of a tube with a connected syringe can make it possible to introduce a staining solution into the receiving chamber. In the process, the medium already available in the receiving chamber can be flushed out or mixed with the staining solution. In an alternative application, the graft or implant can be moved inside the receiving chamber or moved out of the receiving chamber by generating a suction or thrust effect through the connected tube and the connected syringe. For this purpose, a closure device with a grid has to be replaced by a closure device without grid. In a further application, a known cartridge or sleeve can be connected with the receiving device to provide and introduce a graft or implant. Said cartridge or sleeve can be connected with a tube with a syringe so that the graft or implant can be moved into the cartridge or sleeve via a suction or thrust effect caused by actuating the piston of the syringe. All previously mentioned applications can be easily implemented by using appropriate closure devices, collars, adapters or adapter areas. Alternatively, it is also possible to use an appropriate device for supplying and/or discharging the medium and/or a further fluid medium instead of using a syringe.

Advantageously, the receiving device can be produced from plastic material, glass or metal. The material should be selected in accordance with the respective application. For example, a transparent form allows for secure observation and monitoring of the position of the graft or implant arranged in the receiving chamber. A form consisting of glass or metal makes it possible to safely reuse the receiving device, because receiving devices made from these materials are especially easy to clean and/or sterilize. Usually, devices consisting of plastic material are especially cost-effective, but such cases should be considered only for a one-time application.

Furthermore, the above-mentioned problem is solved by a receiving device with the characteristics of the subordinate claim 8. Said receiving device has a respective closure device for both passages, wherein at least one closure device is permeable for the medium. To avoid repetitions, reference is made to the preceding description, which explains the advantages of such a receiving device.

In an especially advantageous manner, one of the two passages can be connected with a cartridge or sleeve, which has openings on its two opposite ends, wherein the first opening has a larger diameter than the second opening. This combination of receiving device and connected cartridge or sleeve does not only allow for a secure support and secure transport of a graft or implant, but also its simple provision for introducing the graft or implant, for example, by means of a syringe, or a device for supplying and/or discharging the medium and/or a further fluid medium, connected with the other passage of the receiving device.

The above-mentioned combination of receiving device and cartridge or sleeve, which includes the graft or implant, can be provided to a surgeon for directly introducing the graft or implant into the human or animal body.

In a further advantageous manner, the cartridge or sleeve can be designed in such a way that the outer edge of the second opening can be inserted into the nozzle of a syringe and/or that the first opening can be mounted on the nozzle of said syringe or on a different syringe. When the outer edge of the second opening is inserted into the nozzle of a syringe, it is possible to produce via the syringe a vacuum, which sucks the graft or implant out of the receiving device connected with the first opening into the cartridge or sleeve. As a result, the sleeve or cartridge can be disconnected from the receiving device and can be mounted with the first opening onto the nozzle of said syringe or a different syringe. Thus the graft or implant is provided to be introduced into the human or animal body. Actuating the syringe can generate an adequate thrust for introducing the graft or implant into the human or animal body.

Alternatively, a syringe can be connected with the end of a receiving device connected with a cartridge or sleeve that is located opposite of the cartridge or sleeve. In this way, a combination of interconnected cartridge or sleeve, receiving device and syringe would be provided. The connection between these three elements can be performed by means of appropriate collars and/or adapters. In this case, the insertion of the piston of the syringe results in a thrust effect on the graft or implant in the receiving chamber of the receiving device so that the graft or implant can be moved into the cartridge or sleeve and can be inserted or injected even further into the human or animal body. In this case, it is not necessary to disconnect the cartridge or sleeve from the receiving device before introducing the graft or implant into the body.

The above-mentioned problem is also solved by means of a set with the characteristics of claim 11. Such a set comprises a device according to any one of the preceding claims, and said device is securely and comfortably provided in sterile condition or in a package suitable for sterilization. To avoid repetitions, reference is made to the preceding description of the inventive device, which explains the advantages of the device comprising the set. The above-mentioned advantageous effects apply in the same manner to the inventive set.

Advantageously, the set can also comprise a syringe and an adapter and/or tube suitable for forming a connection with the device, which allows the components of the set to be applied in ways.

Alternatively and additionally, the receiving device can already contain a graft or implant. In this respect, it is possible in the context of the present invention to provide a set ready for use.

Figure 2:
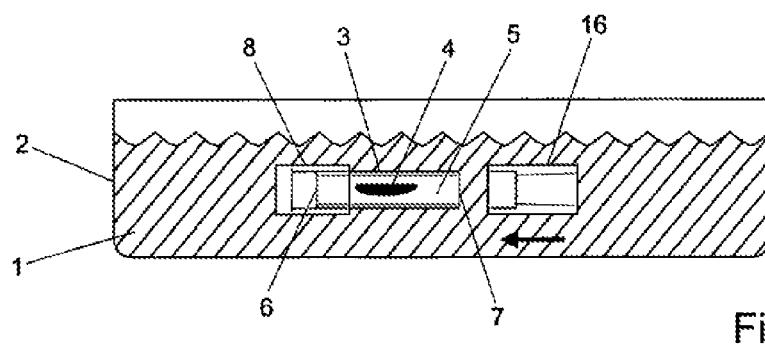
Figure 3:
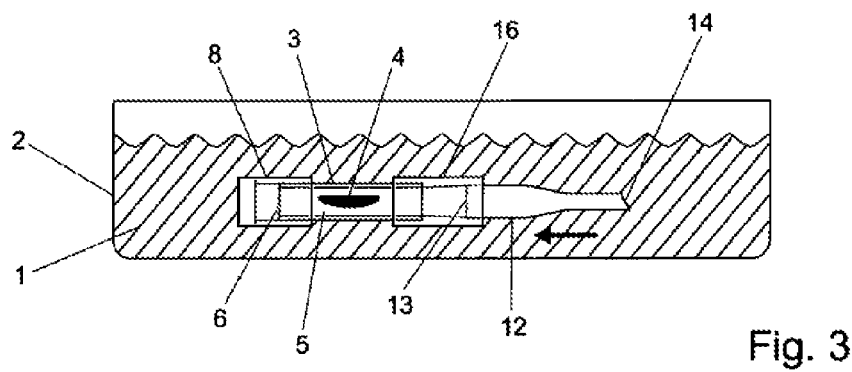
Figure 4:
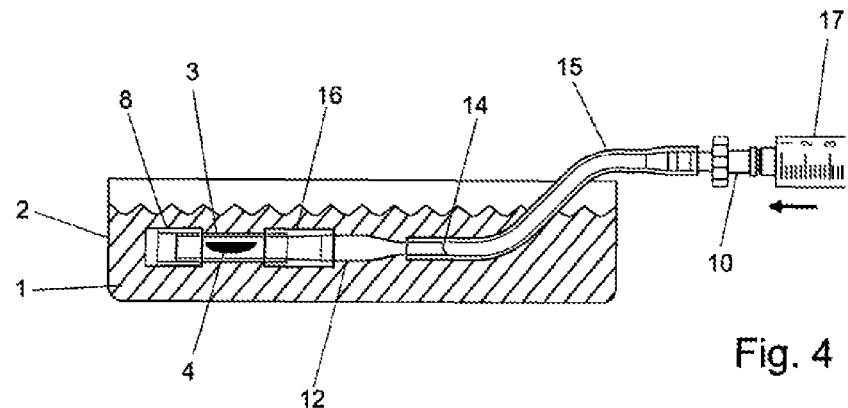
Figure 5:
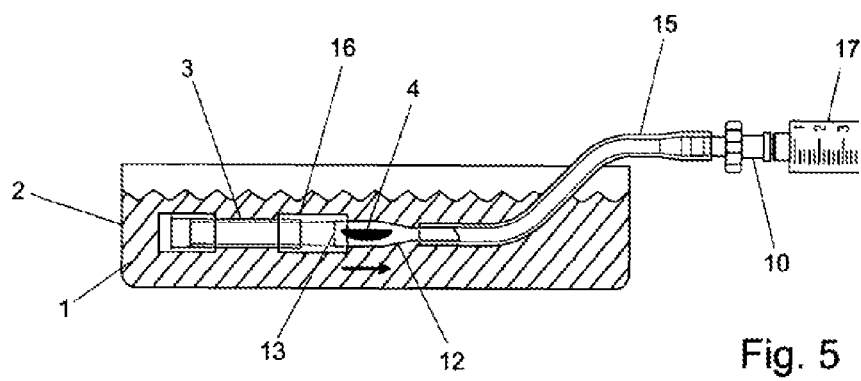
Figure 6:
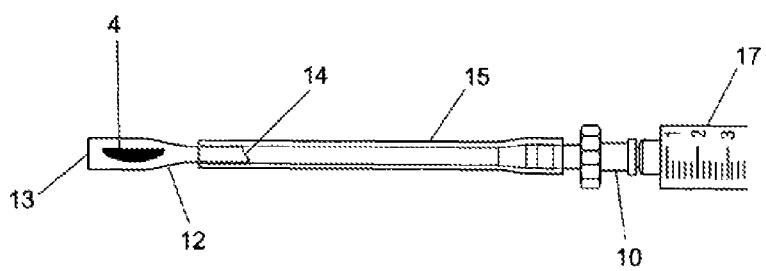
Figure 7:
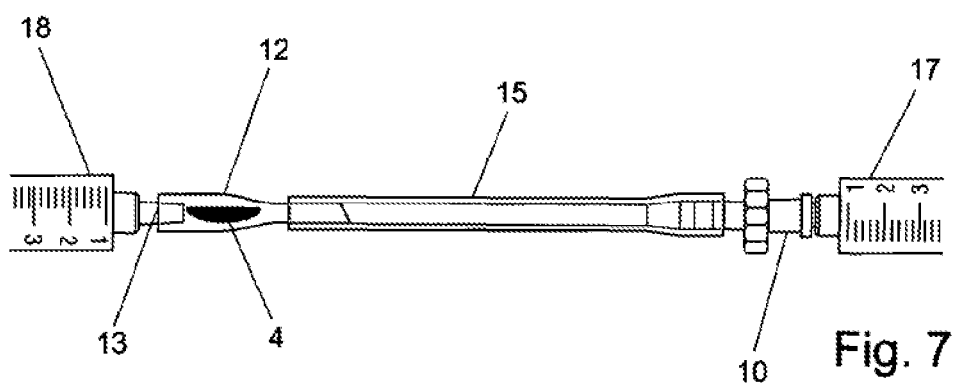
Figure 8:
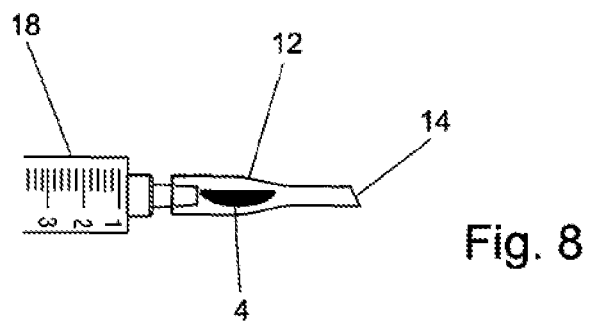
Figure 9:
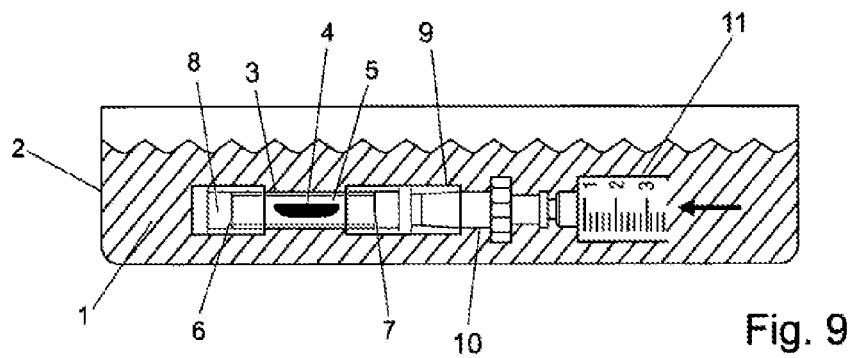
Figure 10:
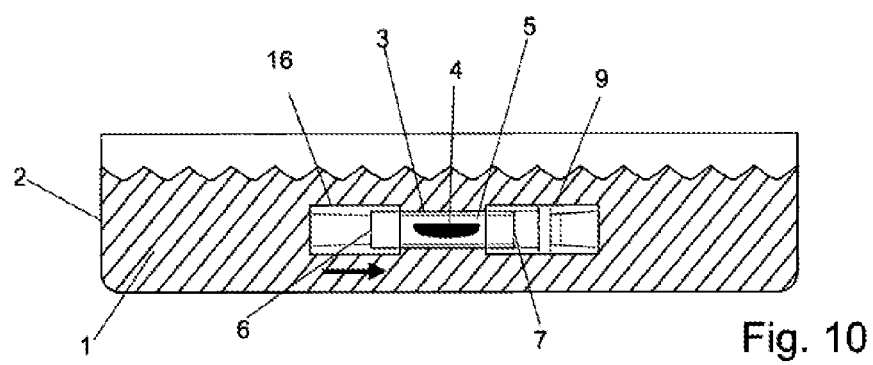
Figure 11:
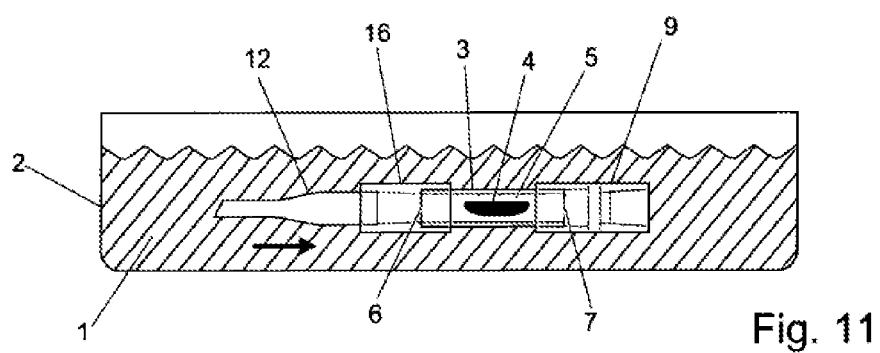
Figure 12:
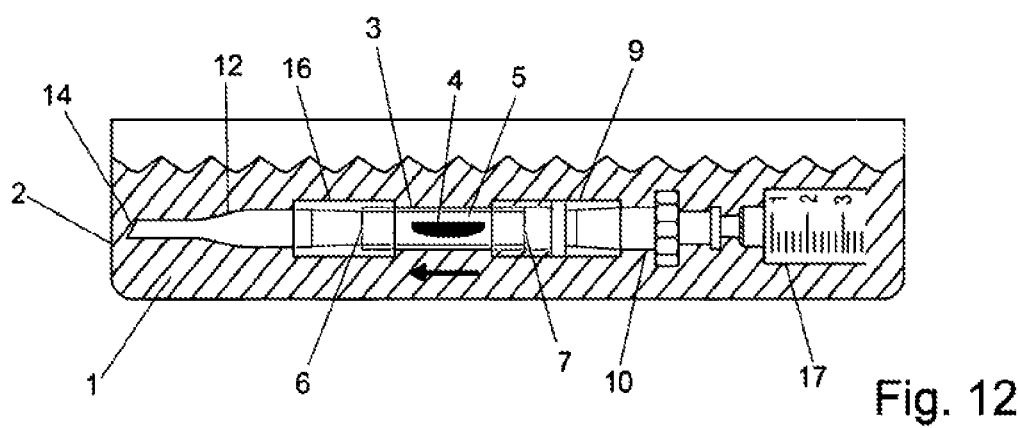

There are different options to arrange and further develop the theory of the present invention in an advantageous manner. For this purpose, reference is made to the subordinate claims and the following description of preferred embodiments of the inventive device, the inventive receiving device and the inventive set. In the context of describing the preferred embodiments by means of the drawing, generally preferred embodiments and further developments of the theory are also described. It is shown:

FIG. 1 a diagram of an embodiment of an inventive device for supporting and transporting a graft or implant with a connected syringe, FIG. 2 a diagram of the embodiment shown in FIG. 1, in which a closure device is replaced with a collar suitable for adaption, FIG. 3 a diagram of a receiving device arranged in the container with the collar connected in the manner shown in FIG. 2 and a cartridge or sleeve connected via the collar for providing and introducing the graft into the body, FIG. 4 a diagram of the arrangement shown in FIG. 3, in which a tube and a syringe are also connected with the cartridge or sleeve, FIG. 5 a diagram of the arrangement shown in FIG. 4, in which the graft has been moved into the cartridge or sleeve by actuating the syringe, FIG. 6 a diagram of the arrangement shown in FIG. 5, in which the receiving device and the collar have been removed from the cartridge, FIG. 7 a diagram of the arrangement shown in FIG. 6, in which a further syringe is inserted into the cartridge, FIG. 8 a diagram of the arrangement shown in FIG. 7, in which the tube is removed from the cartridge, allowing the graft or implant to be introduced by means of the cartridge into the body, FIG. 9 a diagram of the starting point of a further variation for handling the inventive device, wherein this representation corresponds to the representation shown in FIG. 1, FIG. 10 a diagram of the arrangement shown in FIG. 9, in which the syringe with the adapter has been removed and on the opposite side a closure device has been replaced by a collar suitable for adaption, FIG. 11 a diagram of the arrangement shown in FIG. 10, in which a cartridge for providing and introducing the graft into the body is connected with the collar, which is connected according to FIG. 10, and FIG. 12 a diagram of the arrangement shown in FIG. 11, in which an adapter and a syringe is connected with the end of the receiving device facing away from the cartridge, so that the graft or implant can be introduced with this arrangement directly into the body.

FIG. 1 shows a lateral view of an embodiment of an inventive device for supporting and transporting a graft or implant. The device comprises a container 2, which can be filled with a medium 1, and a receiving device 3 for the graft 4 or implant, which can be arranged in the container 2. For the sake of simplicity, we shall subsequently only mention the graft although, alternatively, the same applies to an implant.

The receiving device 3 comprises a receiving chamber 5 for the graft 4 and two passages 6, 7 leading to the receiving chamber 5. The receiving device 3 is designed in the form of a cylinder, so that both passages 6, 7 are dimensioned in such a way that the graft 4 can be introduced and/or removed into or out of the receiving chamber 5. Each of the passages 6, 7 is provided with a closure device 8, 9 and both closure devices 8, 9 are permeable for the medium 1.

To provide the receiving device 3 with the graft 4, the cylinder-shaped receiving device 3 is first closed on one side with a closure device 9, which is permeable for the medium 1 but prevents the graft 4 from passing over. Then, an adapter 10 is connected with the closure device 9 and by means of the adapter 10 a syringe 11 is connected. When pulling the piston out of the syringe 11, the graft 4 is sucked through the still open passage 6. Then, the receiving device 3 is closed with a further closure device 8 at the still open passage 6 and the syringe 11 with the adapter 10 is removed. As a result, the receiving device 3 is provided with the graft 4 and ready to be transported.

In an alternative method, a tube can be connected between the adapter 10 and the closure device 9. As a result, the syringe 11 is not directly connected with the receiving device 3 via the adapter 10 and the closure device 9, but also via the tube.

The container 2 can be designed in the form of a bottle with a bottle closure, for example, a screw cap. Such a container 2 designed in the form of a bottle can be advantageously used for transporting and dispatching the graft 4. Alternatively, the container 2 can also be designed in the form of an open, and possible closable bowl. To handle the receiving device 3 arranged in the container 2 in an easy manner, a handling element, for example, a plastic strip, can be attached at the receiving device 3 or a closure device 8 or 9, with which the receiving device 3 can be simply pulled out of the opening of the container 2 that is designed in the form of a bottle. The handling element can be fixed in the area of the bottle neck or the opening of the bottle, so that it is easy to grab the handling element after removing the bottle closure and pull the receiving device 3 out of the bottle or the container 2. To handle the receiving device 3 in an easy manner, said receiving device 3 can be placed in a bowl after removing it from the container 2. The medium 1 located in the container 2 can also be poured into the bowl. This makes it easy to access the receiving device 3 and the graft 4.

The closure devices 8 and 9 can be mounted on the receiving device 3 and are basically designed in the form of a collar. The closure devices 8 and 9 are produced from an elastic plastic material. Both closure devices 8 and 9 have a grid to provide the permeability for the medium 1 and a further medium. However, said grid prevents the graft 4 from escaping the receiving device 3.

However, FIG. 1 does not show the above-mentioned process of loading the receiving device 3, but the process of staining the graft 4. Usually, different syringes 11 are used for loading and staining the graft 4. The process of loading the receiving device 3, as well as the process of staining the graft 4 are performed in the container 2 filled with the medium 1. The arrow in FIG. 1 indicates that a staining solution is introduced from the syringe 11 via the adapter 10 and the closure device 9 provided with a grid and through the passage 7 into the receiving chamber 5. Because of the fact that both closure devices 8 and 9 are permeable for the medium 1 and the staining solution, but the graft 4 is prevented from escaping the receiving chamber 5 because of the grid, it is possible in a simple and safe manner to stain and flush the graft 4 by actuating the piston of the syringe 11. During the flushing and/or staining process, the whole receiving device 3 and the graft 4 remain in the medium 1.

The closure devices 8 and 9 provided with grids ensure that the medium 1 is adequately circulated throughout the receiving device 3 when the device is transported.

According to FIG. 2, when the staining process is concluded, the closure device 9 is replaced by a collar 16, which has no grid and allows the graft 4 to pass through the passage 7 and the collar 16. For this purpose, the collar 16 is mounted on the receiving device 3, instead of the closure device 9.

According to FIG. 3, in a following step, a sleeve or cartridge 12 known from DE 10 2010 051 458 A1 is inserted into an adapter area of the collar 16 to provide a flow connection from the receiving chamber 5 via the collar 16 into the cartridge 12. The cartridge 12 has a larger opening 13, which is arranged in the collar 16. On the opposite end, the cartridge 12 has an opening 14 with a diameter smaller than opening 13. The end of the cartridge 12 with opening 14 is used for an insertion into an incision to introduce the graft 4 into the human or animal body.

According to FIG. 4, in a following step, a hose 15 is placed over opening 14 of the cartridge 12. An adapter 10 with a syringe 17 is arranged on the other end of the hose 15. The syringe 17 is filled with a fluid, for example, saline solution. It is important to ensure an air-bubble-free connection.

According to FIG. 5, the graft 4 has been moved into the cartridge 12 by carefully retracting the piston of the syringe 17. It is important to ensure that the graft 4 is not sucked in too quickly so as not to be jammed in the narrow part of the cartridge 12, which involves the risk of damaging the graft 4.

All above-mentioned steps are performed while the receiving device 3 is situated in the medium 1.

In a further step, the hose 15 and the collar 16 with the receiving device 3 can be removed from the cartridge 12. Subsequently, the larger opening 13 of the cartridge 12 can be mounted on a nozzle of a syringe. As a result, the cartridge with the graft 4 arranged in it is prepared for introducing the graft 4 into the body.

FIGS. 6 to 8 show a diagram of a variation of a possible application which, starting from the situation shown in FIG. 5 results in mounting a cartridge 12 on a syringe 18. According to FIG. 6, in a particular case, the collar 16 with the receiving device 3 is first removed from the cartridge 12. Then, according the FIG. 7, a further syringe 18 is inserted in the larger opening 13 of the cartridge 12. Subsequently, according to FIG. 8, the hose 15 with the adapter 10 and the syringe 17 is removed from the cartridge 12. The remaining arrangement is now prepared for directly inserting the graft 4 into the body.

As an alternative to the process of introducing the graft 4 into the cartridge, as shown in FIGS. 4 and 5, a syringe, with or without hose, can be connected with the passage 6 of the receiving device 3, according to the situation and arrangement sown in FIG. 3. For this connection of the syringe, it is preferred that the closure device 8 is replaced with an appropriate collar or adapter, which is permeable for a medium 1 or different fluid. In this alternative embodiment, the graft 4 can be moved through the collar 16 and opening 13 of the cartridge 12 into the cartridge 12 by adequately pushing the piston of the syringe, which is connected in the area of the passage 6. As a result, the graft 4 is also prepared for being introduced into the body by means of the cartridge 12 and its smaller second opening 14. In this second provision, it is possible to eliminate a separate introduction or loading of the graft 4 into the cartridge 12, like it was described in the above-mentioned case demonstrated in FIGS. 4 and 5. By simply connecting an appropriate syringe at the end of the receiving device 3 located opposite of the cartridge 12, the basis is provided for introducing the graft 4 into the body by means of the cartridge 12.

According to a further embodiment, the final arrangement described in the previous paragraph can also result in the succession of steps shown in FIGS. 9 to 12. The succession of steps is based on the arrangement shown in FIG. 9, which corresponds to the arrangement shown in FIG. 1.

According to FIG. 10, closure device 8 is replaced by a collar 16, and the adapter 10 and the syringe 11 are removed from closure device 9.

According to FIG. 11, a cartridge 12, which is described above in detail, is connected with the collar 16.

Finally, according to FIG. 12, an adapter 10 with a further syringe 17 is connected with the closure device 9. This allows the graft 4 to be moved by pushing the piston of the syringe 17 into the cartridge 12 and subsequently introducing the graft 4 into the body.

The inventive device for supporting and transporting a graft 4 allows for loading the graft into the receiving device 3 and allows for a secure support and/or transport in the container 2.

For example, the following parts are required for loading the receiving device 3: the receiving device 3, a closure device 9 with grid closure and an adaption area for connecting a hose 15 and/or a syringe 11, wherein each end of said hose is provided with an adapter 10, and a syringe 11. The closure device 9 can be designed in the form of a collar with grid and flushing attachment. It is possible to insert an adapter 10 for the hose 15 or syringe 11 into the flushing attachment.

Basically, both above-mentioned variations can be used for introducing the graft 4 into the body.

For variation 1 the following parts are required: closure device 8, involving the collar with grid closure, receiving device 3, collar 16 without grid closure, cartridge 12, hose 15 with adapter 10 and syringe 17.

For variation 2 the following parts are required: cartridge 12, collar 16 without grid closure, receiving device 3, closure device 9 with grid closure and adapter area for inserting the adapter, said adapter and syringe.

Advantageous embodiments of the inventive device can comprise components according to the following variations:

Variation 1:
8 collar with grid closure
3 receiving device
9 collar with grid closure for adapter 10 and syringe 11
16 collar without grid closure replaces the collar 9
12 cartridge
15 hose
10 adapter
11 syringe
17 syringe Variation 2:
8 collar with grid closure
3 receiving device
9 collar with grid closure for adapter 10 and syringe 11
16 collar without grid closure replaces the collar 8
12 cartridge
10 adapter
17 syringe With regard to handling the receiving device 3 arranged in the container 2 and thus in the medium 1, which receiving device 3 is provided with a graft 4, a surgeon is completely flexible in his actions. For example, in the context of different previously described embodiments, he can perform the connecting and disconnecting steps of the above-mentioned components of the receiving device 3 arranged in the container 2 and thus in the medium 1. Alternatively, depending on the requirements, he can remove the receiving device 3 with the graft 4 arranged in said receiving device from the medium 1 and, if required, return it into the medium 1 after connecting and/or disconnecting processes. A surgeon can freely choose his action, depending on the requirements and/or his preference.

Regarding further embodiments of the inventive device, the inventive receiving device and the inventive set and for the purpose of preventing repetitions, reference is made to the general portion of the description and the enclosed claims.

It should be emphasized that the embodiments described above only have the purpose of discussing the theory claimed but the embodiments are not limited to said theory.

REFERENCE LIST

1 medium
2 container
3 receiving device
4 graft
5 receiving chamber
6 passage
7 passage
8 closure device
9 closure device
10 adapter
11 syringe
12 cartridge
14 opening
15 hose
16 collar
17 syringe
18 syringe

The invention claimed is:

1. A device for supporting and transporting a graft consisting of a Descemet membrane with a healthy corneal endothelium, comprising:
a container comprising a medium, and
a receiving device arranged in the container and submerged within the medium, wherein the receiving device is in the form of a sleeve or cylinder having a first end and a second end and a receiving chamber therebetween to receive the graft and two passages formed by a first opening at the first end and a second opening at the second end which lead to the receiving chamber, at least one of said passages being dimensioned for introducing or removing the graft into or out of the receiving chamber, and a respective closure device for each of the two passages, wherein at least one of the closure devices is permeable for the medium and wherein one of the two closure devices is formed through a constriction of the receiving device or a passage and is implemented as an integral component of the receiving device, and
wherein the graft can be moved inside the receiving chamber or moved out of the receiving chamber by generating a suction or thrust effect through a syringe or through a device for supplying and/or discharging the medium.

2. A device according to claim 1, characterized in that the other closure devices is mountable on the receiving device and shaped in the form of a collars.

3. A device according to claim 1, characterized in that the other closure devices is made of a slightly elastic material.

4. A device according to claim 1, characterized in that the other closure devices comprises a grid to provide the permeability for the medium.

5. A device according to claim 1, characterized in that the receiving device or at least one of the two closure devices is designed with a provision for connecting a collar or an adapter to a tube, a syringe, or a device to supply or discharge the medium or a further fluid medium.

6. A device according to claim 1, characterized in that the receiving device is made from a transparent plastic material, glass or metal.

7. A device according to claim 1, characterized in that one of the two passages is connected with a cartridge or sleeve which has openings on its two opposite ends, wherein the first opening of the cartridge has a larger diameter than the second opening of the cartridge.

8. A device according to claim 7, characterized in that the outer edge of the second opening of the cartridge is insertable into a nozzle of a syringe.

9. A set, comprising the device for supporting and transporting a graft according to claim 1 in sterilized condition or in a package suitable for sterilizing.

10. A set according to claim 9, characterized in that the set further comprises a syringe and an adapter or hose suitable for forming a connection with the device for supporting and transporting a graft.

11. A device according to claim 3, wherein the slightly elastic material is a plastic material.

12. A device according to claim 5, wherein the fluid medium is a staining solution.

13. A device according to claim 7, wherein the first opening of the cartridge is mountable to a nozzle of a syringe or to a different syringe.

* * * * *